US008747345B2

(12) United States Patent
Salloum

(10) Patent No.: US 8,747,345 B2
(45) Date of Patent: Jun. 10, 2014

(54) PERCUTANEOUS COLLATERAL BYPASS

(75) Inventor: Joseph G Salloum, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 25 days.

(21) Appl. No.: 13/096,597

(22) Filed: Apr. 28, 2011

(65) Prior Publication Data
US 2011/0270148 A1 Nov. 3, 2011

Related U.S. Application Data

(60) Provisional application No. 61/329,471, filed on Apr. 29, 2010.

(51) Int. Cl.
A61F 2/06 (2013.01)
(52) U.S. Cl.
USPC .............................. 604/8; 623/1.11; 623/1.21

(58) Field of Classification Search
USPC .................... 604/8, 500, 506–510; 623/1.36, 623/1.14–1.23; 606/7, 8
See application file for complete search history.

(56) References Cited

U.S. PATENT DOCUMENTS

| 5,980,532 | A | * | 11/1999 | Wang | 623/1.11 |
| 7,473,271 | B2 | * | 1/2009 | Gunderson | 623/1.12 |
| 7,481,790 | B2 | * | 1/2009 | Roorda | 604/103.08 |
| 8,197,528 | B2 | * | 6/2012 | Colgan et al. | 623/1.11 |
| 2006/0190075 | A1 | * | 8/2006 | Jordan et al. | 623/1.23 |
| 2009/0099643 | A1 | * | 4/2009 | Hyodoh et al. | 623/1.15 |

* cited by examiner

Primary Examiner — Philip R Wiest
Assistant Examiner — Benjamin Klein
(74) Attorney, Agent, or Firm — Tarolli, Sundheim, Covell & Tummino LLP

(57) ABSTRACT

A bypass provided by a bypass conduit disposed in a vessel which is collateral to an occluded vessel. The bypass conduit comprises a helical wire body having a plurality of connectors connecting adjacent turns of the helical body.

12 Claims, 21 Drawing Sheets

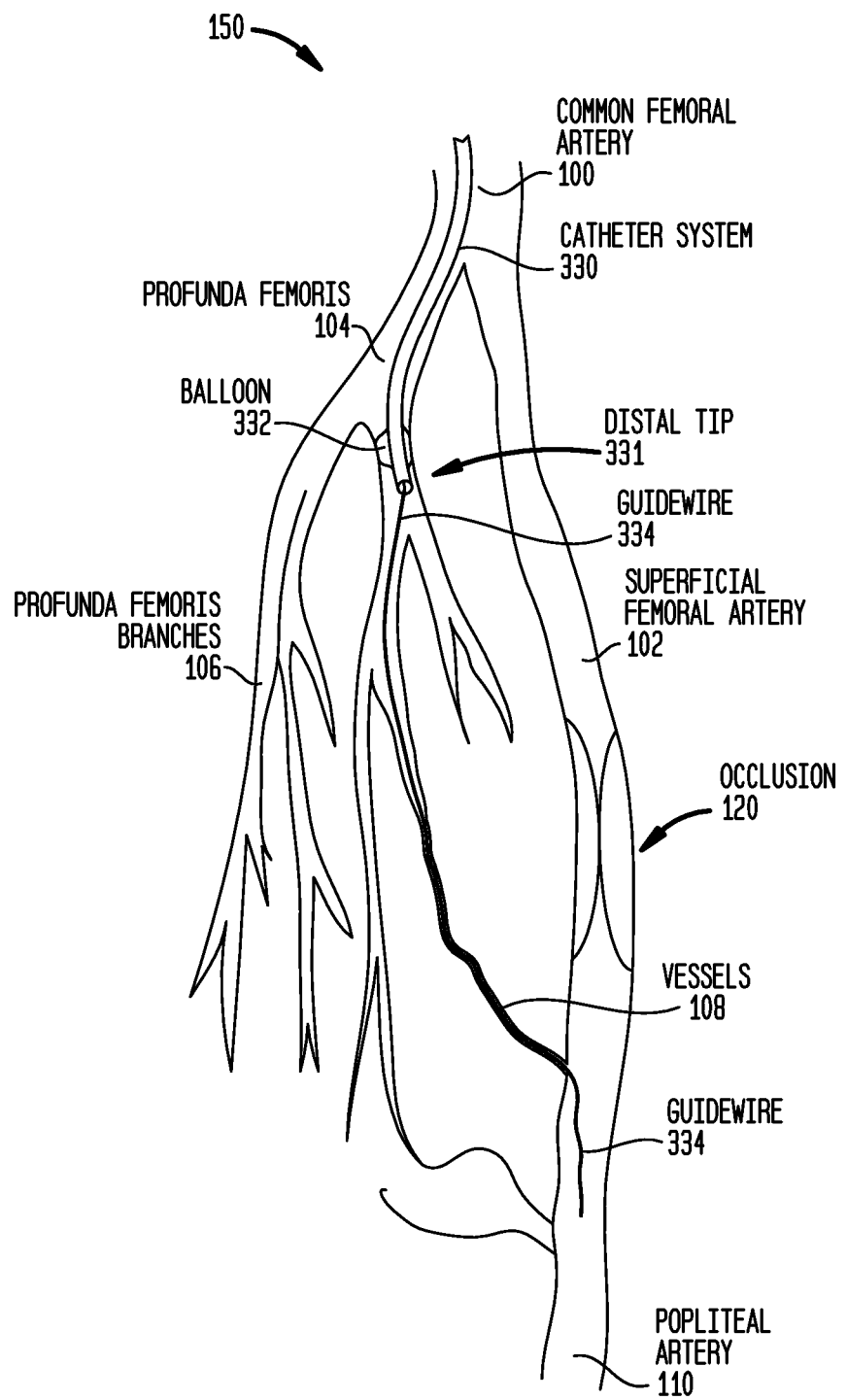

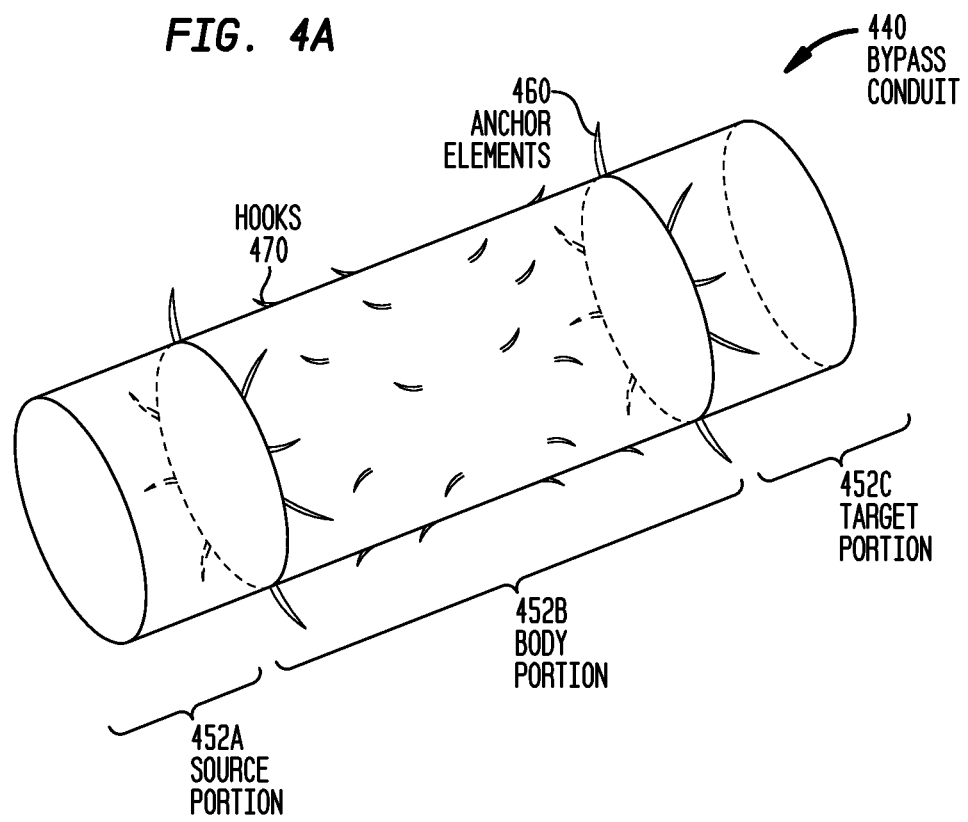

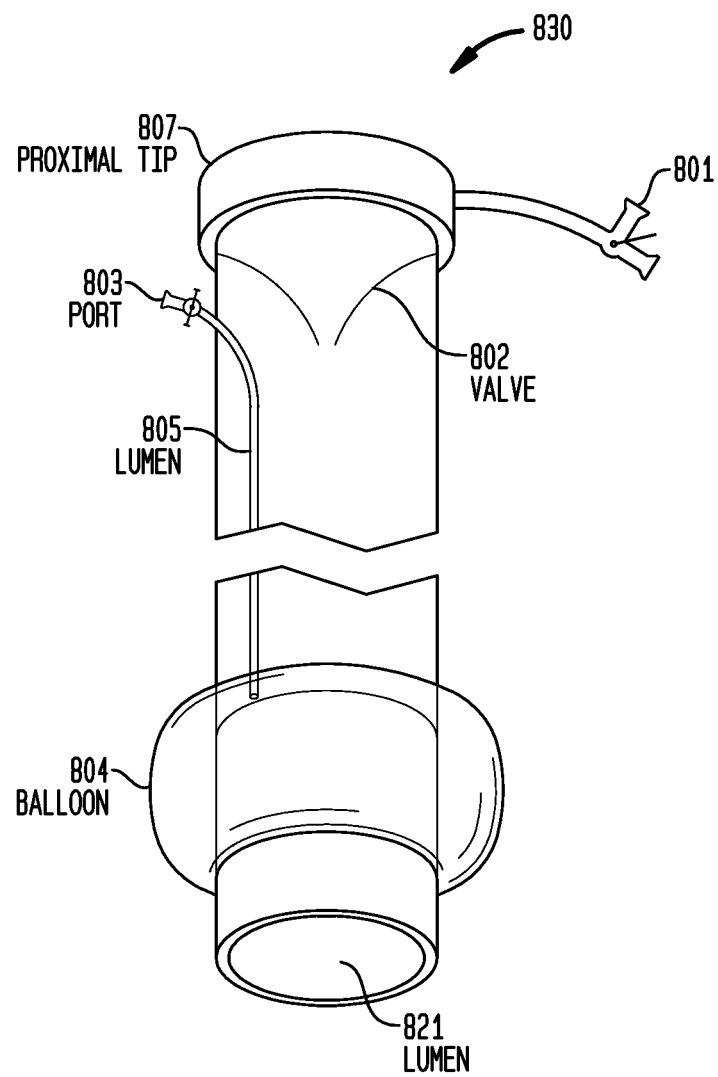

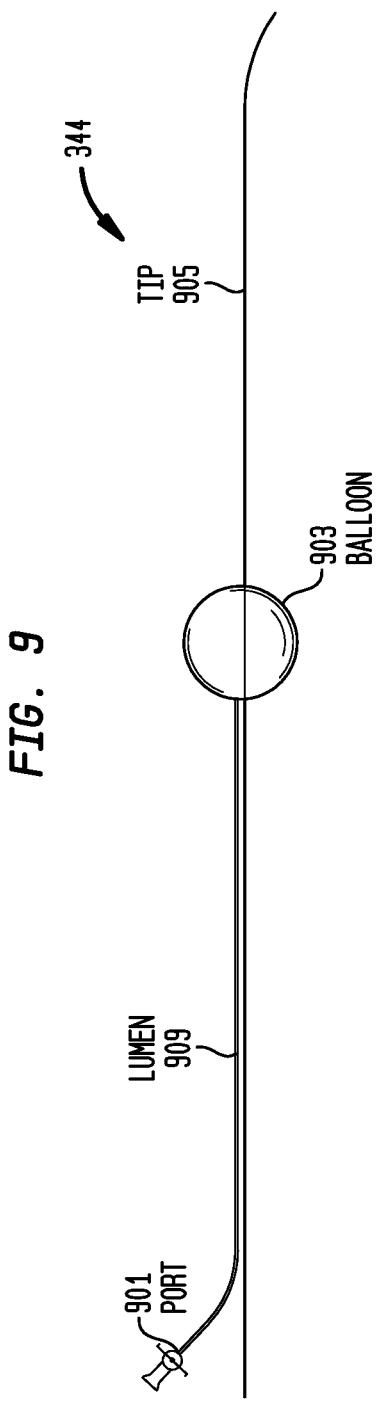

PERCUTANEOUS COLLATERAL BYPASS

CROSS-REFERENCE TO RELATED APPLICATIONS

This application claims priority to U.S. Provisional Patent Application No. 61/329,471, filed Apr. 29, 2010. The content of this application is hereby incorporated by reference herein.

BACKGROUND

1. Field of the Invention

The present invention relates generally to a cardiovascular system bypass, and more particularly, to a percutaneous collateral bypass.

2. Related Art

Patients suffer from a number of different conditions that affect their heart, blood vessels and other regions of their cardiovascular system. Such conditions, generally referred to herein as cardiovascular diseases (CVD), include peripheral vascular disease (peripheral artery disease and peripheral venous disease), aneurysm, atherosclerosis, coronary heart disease, coronary artery disease, ischemic heart disease, cerebrovascular disease, etc. A variety of different procedures are available to doctors, surgeons or other healthcare professionals (collectively referred to as "surgeons" herein) for the treatment of cardiovascular diseases. Such procedures broadly fall into one of two categories: open surgical procedures or minimally invasive endovascular procedures. Open surgical procedures involve the cutting of large incisions in the skin and tissue to provide the surgeon with direct access to a target region of the cardiovascular system. Such procedures are highly invasive and typically require relatively lengthy hospital stays and recovery times. Furthermore, open surgical procedures have a relatively high risk of morbidity and mortality stemming from complications occurring during the procedure.

In minimally invasive or percutaneous endovascular surgical procedures, a patient's cardiovascular system is accessed through relatively small incision(s) in the skin or through an anatomical opening. A percutaneous procedure typically involves the use of laparoscopic or catheter systems which are inserted into the small incision(s), and which are operated remotely by the surgeon. In a percutaneous procedure the surgeon indirectly observes the surgical field through an endoscope separate from, or incorporated in, the catheter system, or by using an imaging device external to the recipient. Due to the minimally invasive access, the patient's hospital stay and recovery times are generally significantly shorter than open surgical procedures.

SUMMARY

In one aspect of the invention, a bypass conduit for implantation into a vessel of a patient's cardiovascular system is provided. The bypass conduit comprises: a helical wire body having a plurality of contiguous, adjacent turns configured to maintain patency of the vessel; and a plurality of connectors connecting adjacent turns of the wire body.

In another aspect of the invention, a method for performing a percutaneous bypass of an occluded blood vessel is provided. The method comprises: expanding a selected collateral vessel to receive at least one bypass conduit comprising a helical wire body having connectors connecting adjacent turns of the helical body; and implanting the at least one bypass conduit into the prepared collateral vessel so that the bypass conduit maintains a patency which is sufficient to substitute for the occluded vessel.

BRIEF DESCRIPTION OF THE DRAWINGS

Illustrative embodiments of the present invention are described herein with reference to the accompanying drawings, in which:

FIG. 3A is schematic view of the region of the cardiovascular system of FIG. 1B illustrating the location of the tip of a catheter system upstream from a selected collateral vessel, in accordance with embodiments of the present invention;

FIG. 4A is a side view of a bypass conduit, in accordance with embodiments of the present invention;

FIG. 8 is a top view of a delivery catheter which may be implemented with embodiments of the present invention;

FIG. 9 is a side view of a support wire and incorporated occlusion balloon which may be implemented with embodiments of the present invention.

DETAILED DESCRIPTION

Embodiments of the present invention are generally directed to systems and methods for performing a percutaneous bypass of a diseased or occluded vessel within a patient's cardiovascular system. The bypass is provided by a generally tubular structure, referred to herein as a stent or bypass conduit, disposed in a vessel which is collateral to the occluded vessel. The bypass conduit comprises a helical wire body having a plurality of adjacent turns that are connected to one another by loop or Z-shaped connectors. In certain embodiments, the loop connectors have a generally elliptical shape.

As noted above, there are a number of cardiovascular diseases that may affect different regions of a patient's cardiovascular system. It would be appreciated that embodiments of the present invention may be used to treat any such diseases, congenital conditions, injuries or other circumstances that cause an interruption in blood flow in a variety of vascular regions or territories. For ease of description and for clarity, embodiments of the present invention will be described herein with reference to a particular cardiovascular disease, namely, atherosclerosis.

Figure 1A:
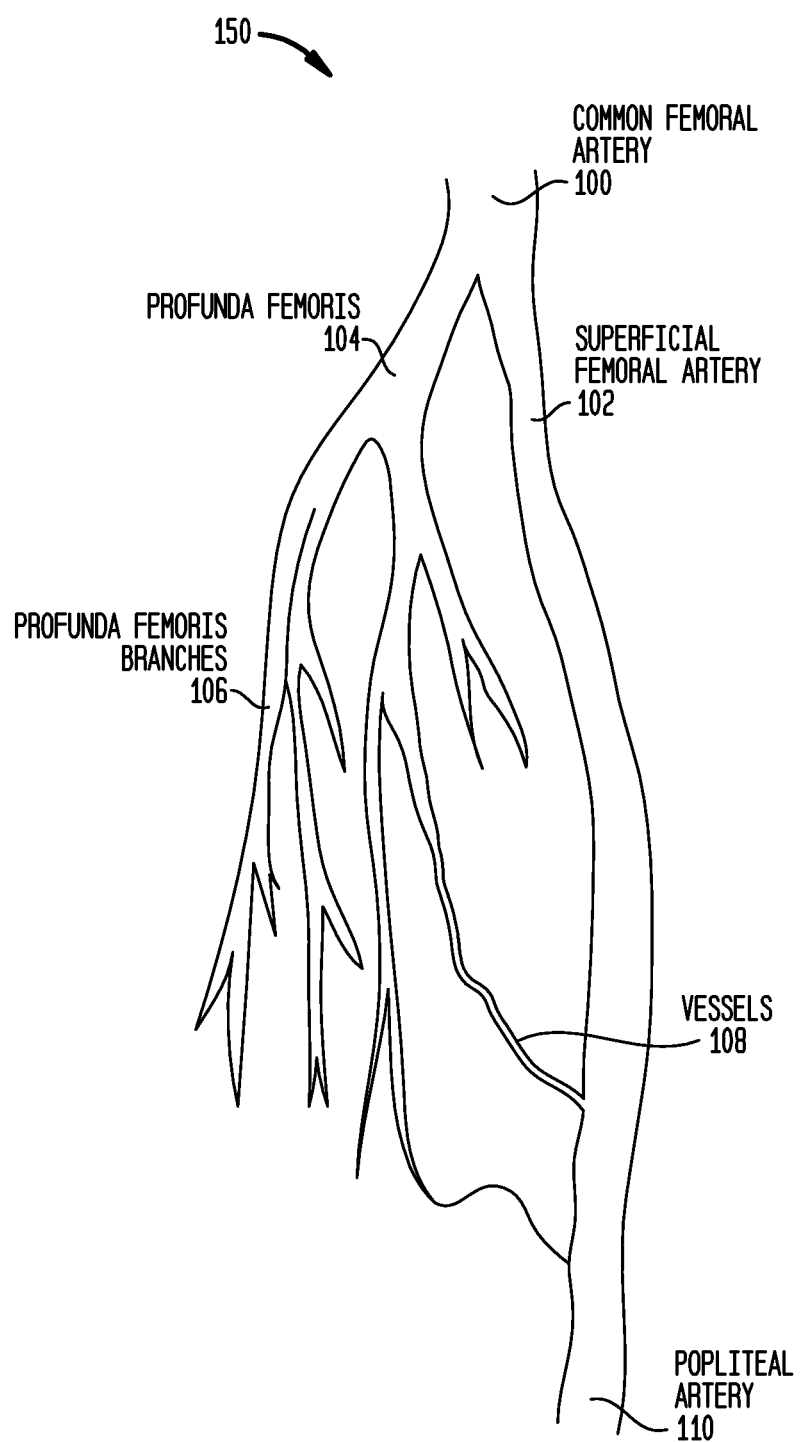
FIG. 1A is a schematic view of a healthy region of a patient's cardiovascular system in which embodiments of the present invention may be implemented upon occurrence of vascular disease within the region.

As is well known, atherosclerosis is the narrowing or obstruction, collectively referred to as occlusion, of blood vessels. A specific type of atherosclerosis which results in the narrowing or obstruction of peripheral blood vessels is known as peripheral vascular disease (PVD). In certain circumstances, PVD occurs in the arteries of a patient's thigh. FIG. 1A is a schematic view of a healthy right thigh region 150 of a patient. As shown, illustrative region 150 comprises the primary vessels located in the thigh, including the common femoral artery (CFA) 100 from which blood flows into the superficial femoral artery (SFA) 102 and profunda femoris (PF) 104. SFA 102 continues into politeal artery 110. As shown, PF 104 includes a plurality of branches 106 which supply blood to the muscles and tissue of the thigh. PF 104 further includes one or more vessels 108 which are generally parallel to SFA 102, and which directly or indirectly enter SFA 102 or politeal artery 110. Such vessels are referred to herein as collateral vessels 108 because the vessels may be prepared to provide a pathway for blood flow that bypasses SFA 102.

Figure 1B:
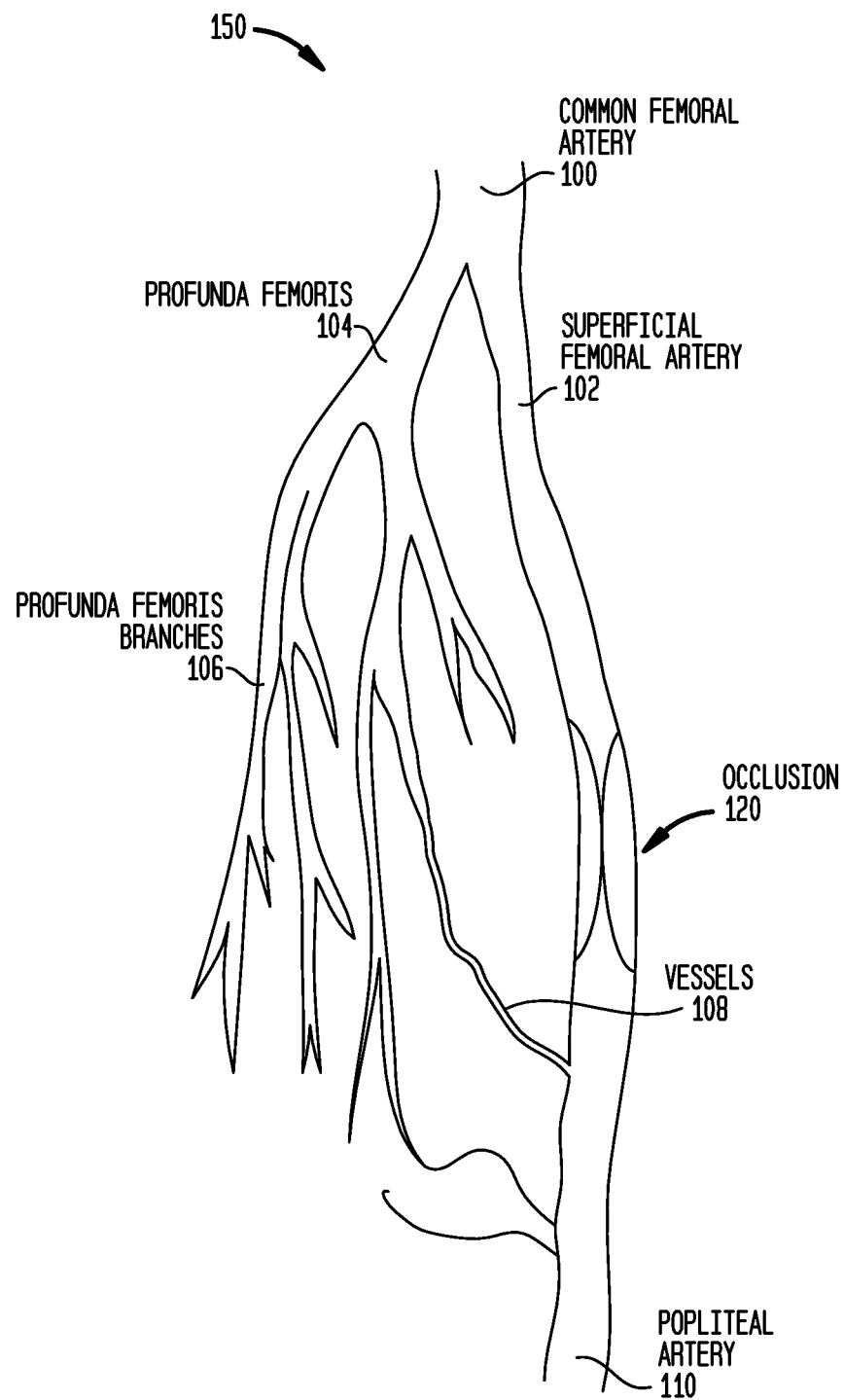
FIG. 1B is a schematic view of the cardiovascular system region of FIG. 1A in which a segment of a vessel is occluded as a result of cardiovascular disease.
Figure 2A:
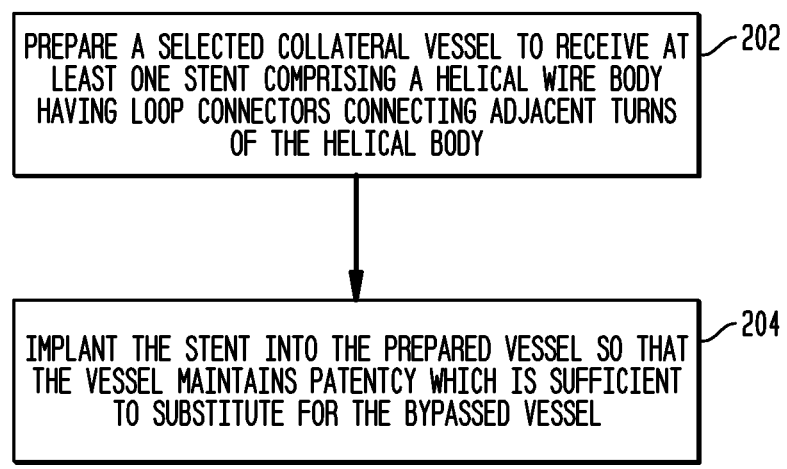
FIG. 2A is a high level flowchart illustrating an exemplary surgical procedure for performing a collateral bypass in accordance with embodiments of the present invention.

FIG. 1B is a schematic view of right thigh region 150 suffering from PVD. As shown, SFA 102 has an occlusion 120 therein that restricts the flow of blood to the lower region of the patient's right leg. As such, a suitable supply of blood to this lower region is needed. FIG. 2A is a high level flowchart illustrating an exemplary percutaneous surgical procedure 200 for preparing a bypass around occlusion 120 in SFA 102 using a selected collateral vessel 108.

Procedure 200, which is implemented as a percutaneous or minimally invasive surgical procedure, begins at block 202 wherein a selected collateral vessel 108 (FIG. 1A) is expanded and/or otherwise prepared to accept a bypass conduit. An exemplary bypass conduit implanted in the selected collateral vessel comprises a helical wire body having a plurality of adjacent turns which are coupled to one another by loop connectors. Further details of an exemplary bypass conduit are provided below with reference to FIGS. 4-5F. Further details of expanding collateral vessel 108 are provided below with reference to FIGS. 2B and 3A-3C.

As would be appreciated, a number of vessels 108 may be collateral to SFA 102. Collateral vessels 108 are usually very small in diameter and allow enough blood flow to sustain tissues downstream from occlusion 120, but do not allow enough blood flow for normal function of the downstream tissues and organs. For example, if an occlusion is present in the vessels of the leg as shown in FIG. 1B, collateral vessels 108 allow enough blood flow to sustain downstream tissues of the leg and foot, but do not allow the patient to walk without problems. Similarly, within the heart, collateral vessels allow the heart muscle to survive, but do not offer complete protection against heart attacks. As used herein, downstream refers to tissues and vessels of the cardiovascular system located between the occlusion and the heart through which blood must flow before returning to the heart.

As previously noted, aspects of the present invention are directed to using the collateral vessels as a track or channel for implantation of a sufficiently large tubular structure to provide adequate blood flow around an occlusion. Specifically, as described below, the selected collateral vessel is prepared and/or expanded to receive the bypass conduit. Preparation of the vessel essential forms a track or channel that receives the bypass conduit. In embodiments of the present invention, preparation of a selected collateral vessel substantially destroys the vessel. This destruction results from the fact that a collateral vessel, in the leg or heart for example, is approximately a fraction of a millimeter in diameter while the bypass conduit may be approximately a few millimeters or a few centimeters in diameter.

In embodiments of the present invention, a collateral vessel 108 is selected because it may be prepared to bypass the occlusion by providing a blood flow pathway which is generally parallel to the occluded section of SFA 102, and which enters SFA 102 or popliteal artery 110 below or downstream from occlusion 120. That is, collateral vessel 108 enters SFA 102 or popliteal artery at a point in the cardiovascular system between the occlusion and the heart through which blood must flow before returning to the heart. A suitable collateral vessel may be selected prior to surgery using, for example, external imaging devices.

Returning to FIG. 2A, procedure 200 continues at block 204 where the bypass conduit is implanted into the prepared selected collateral vessel 108. As used herein, implantation of the bypass conduit into the selected collateral vessel means implantation of the vessel into the track or channel defined by the collateral vessel. That is, the bypass conduit is implanted into the remnants of the selected collateral vessel following preparation. As a result of the implantation, selected collateral vessel 108 maintains patency which is sufficient to substitute for occluded SFA 102. In other words, when implanted, the bypass conduit provides a sufficient flow of blood to the patient's lower right leg so that the effects of PVD are substantially reduced or eliminated. Further details of implanting an exemplary bypass conduit into collateral vessel 108 are provided below with reference to FIGS. 3D-3E.

Figure 2B:
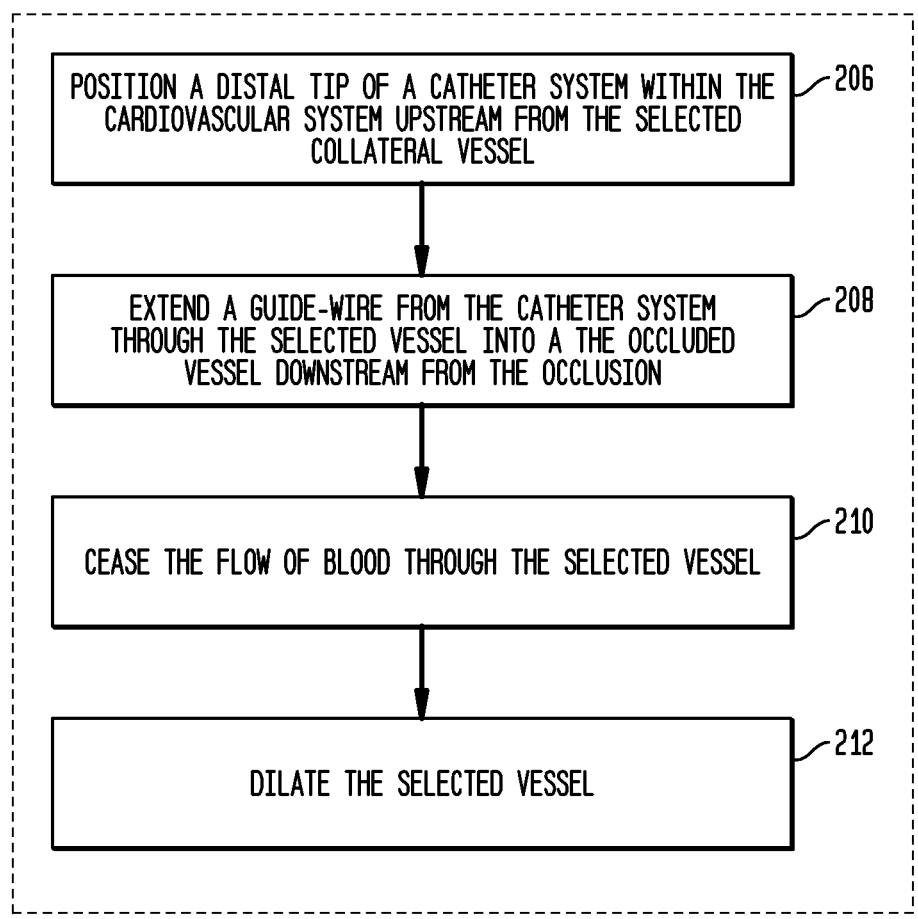
FIG. 2B is a detailed flowchart illustrating operations performed in one exemplary step of an embodiment of the procedure of FIG. 2A.

FIG. 2B is a detailed flowchart illustrating exemplary steps performed during step 202 of method 200 for preparation of selected collateral vessel 108 to accept a bypass conduit. The steps of FIG. 2B will be described with reference to FIGS. 3A-3C which schematically illustrate the preparation of selected collateral vessel 108.

The exemplary method of FIG. 2B commences at block 206 where the distal tip of a catheter system is positioned within the cardiovascular system upstream from selected collateral vessel 108. As used herein, upstream from the collateral vessel, with reference to arterial disease refers to a point in the cardiovascular system between the heart and the collateral vessel through which blood must flow before reaching the collateral vessel. In the case of venous occlusive disease, upstream from the collateral vessel refers to a point in the venous system between the heart and the collateral vessel through which blood flows after having gone through the collateral vessel.

FIG. 3A illustrates an exemplary position of a distal tip 331 of a catheter system 330. In the embodiments of FIG. 3A, catheter system 330 is percutaneously introduced into the patient via a vascular site such as, in this specific implementation, CFA 100. Following implantation, tip 331 is advanced into PF 104 upstream of selected collateral vessel 108.

Returning to the method of FIG. 2B, at block 208 a guide-wire 334 (FIG. 3A) is advanced from catheter system 330 through selected collateral vessel 108. As shown in FIG. 3A, guide-wire 334 advances into SFA 102 at a point downstream from occlusion 120.

After advancement of guide-wire 334, the surgeon interrupts the flow of blood through selected collateral vessel 108. In the exemplary embodiment of FIG. 3A, the flow of blood through collateral vessel 108 is ceased by inflating occlusive balloon 332 positioned at distal tip 331 of catheter system 330. In such embodiments, balloon 332 surrounds a section of tip 331 to form a substantially fluid tight seal with the walls of PF 104. The interruption of blood flow provides hemostasis and prevents internal bleeding while the procedure is being carried out.

Figure 3B:
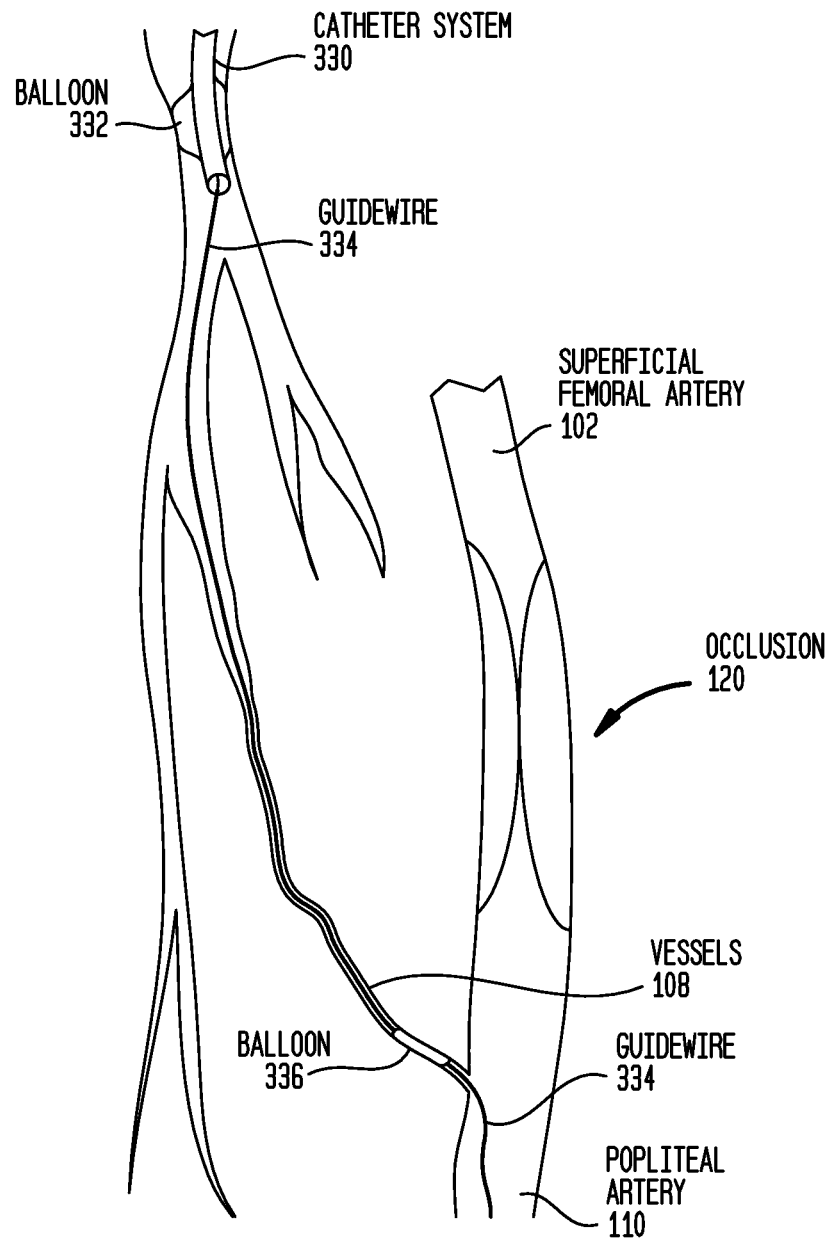
FIG. 3B is schematic, further enlarged view of only a portion of the cardiovascular region of FIG. 3A illustrating a first dilation of the selected vessel, in accordance with embodiments of the present invention.

At block 212, selected collateral vessel 108, and surrounding tissues, are dilated so that the bypass conduit may be implanted in the channel defined by the vessel. FIG. 3B illustrates one exemplary method for preparing dilating collateral vessel 108. It would be appreciated that other methods for preparing and dilating collateral vessel 108 may implemented in alternative embodiments of the present invention. As shown in FIG. 3B, in certain embodiments a balloon 336 is extended from catheter system 330 over guide wire 334 in order to sequentially dilate collateral vessel 108. That is, deflated balloon 336 is first implanted into the section of vessel 108 most proximate to catheter system 330, and then expanded to dilate that section. Balloon 336 is then deflated, advanced into the next adjacent section of collateral vessel 108, and expanded. This procedure is repeated until SFA 102 is reached. In certain embodiments, the side wall of target vessel 110 is also dilated to allow the deployment and expansion of the bypass conduit. In an alternative embodiment, balloon dilatations may be performed by placing the balloon distally first, then sequentially dilating sections in the direction of catheter 330. For ease of illustration, the connection between balloon 336 and catheter system 330 have been omitted.

Figure 3C:
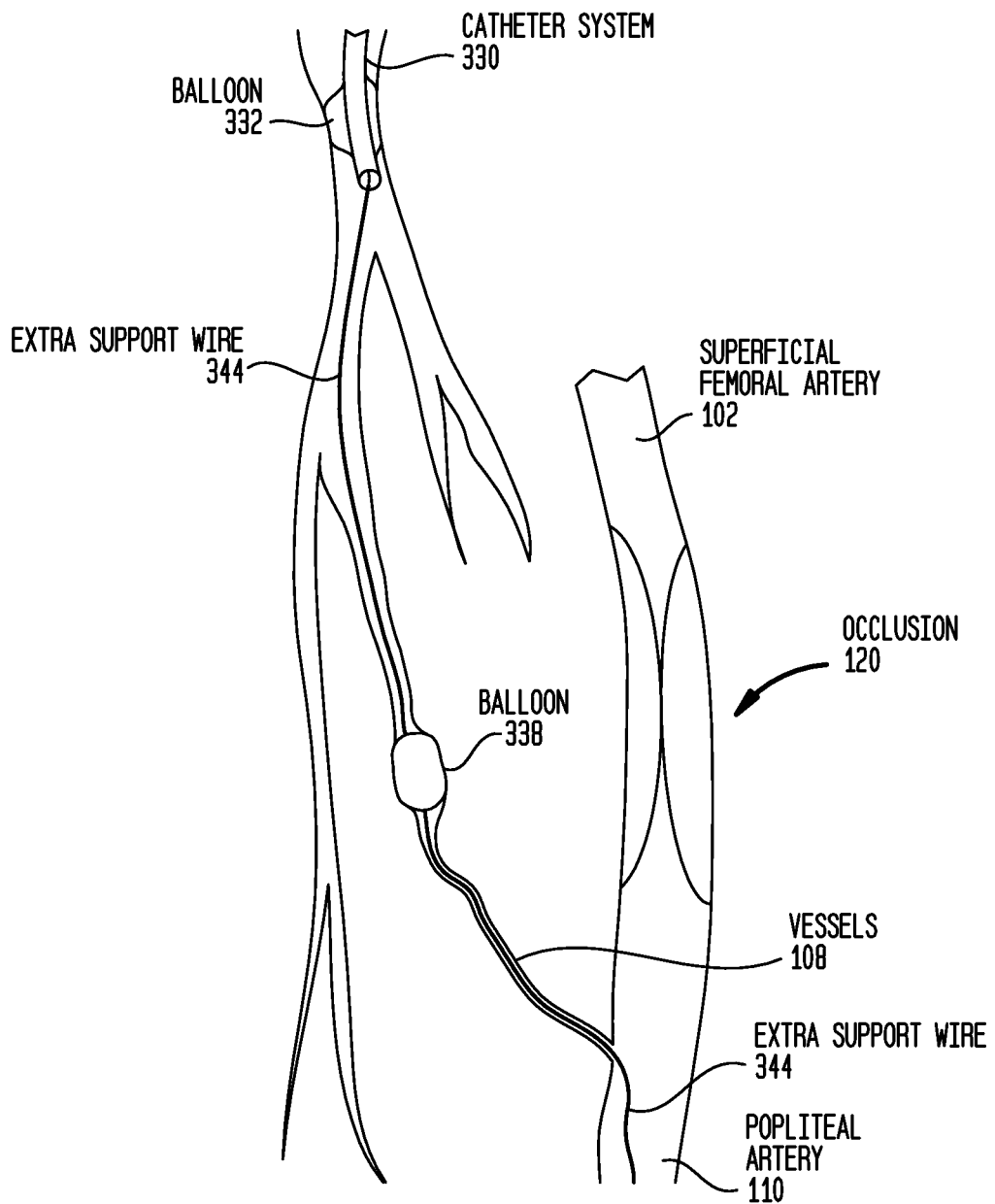
FIG. 3C is schematic, further enlarged view of only a portion of the cardiovascular region of FIG. 3A illustrating a second dilation of the selected vessel, in accordance with embodiments of the present invention.

In certain embodiments of the present invention, selected collateral vessel 108 is further dilated through the use of a second balloon 338. Specifically, as shown in FIG. 3C, balloon 336 is removed, and a relatively larger balloon 338 is used to sequentially further dilate collateral vessel 108. Prior to, during, or after this second dilation, guide-wire 334 may be replaced with an extra support wire 344. For ease of illustration, the connection between balloon 338 and catheter system 330 have been omitted.

As would be appreciated, dilation of selected collateral vessel 108 may result in the dislodgement of tissues or other materials from the vessel. Such dislodged materials could create additional occlusions within the cardiovascular system, or cause serious complications if allowed to reach the heart. As such, in certain embodiments, a screen or other apparatus for collecting such materials may be placed downstream from collateral vessel 108. For ease of illustration, the use of such a screen has not been shown in FIG. 3B.

Additionally, dilation of selected collateral vessel 108 and/or target vessel 110 may result in back bleeding from the target vessel. More specifically, during creation of the channel for the bypass conduit, target vessel 110 continues to receive blood flow from other collateral vessels. Blood in the target vessel 110 may bleed back into the procedural field. The support wire 334 with an incorporated balloon 338 allows the surgeon to obturate (or plug up) the side wall of the target vessel in order to prevent back bleeding into the surgical field. Once the bypass conduit is deployed, the wire incorporated balloon can be deflated to allow blood to flow through the conduit.

As noted, FIG. 3C illustrates embodiments in which a second balloon is used to further dilate collateral vessel 108. It would be appreciated that other methods for dilating collateral vessel 108 may also be implemented. For example, in one embodiment a tissue dissector may be used to further dilate collateral vessel 108. An exemplary tissue dissector is described in greater detail below with reference to FIGS. 7A and 7B.

Figure 3D:
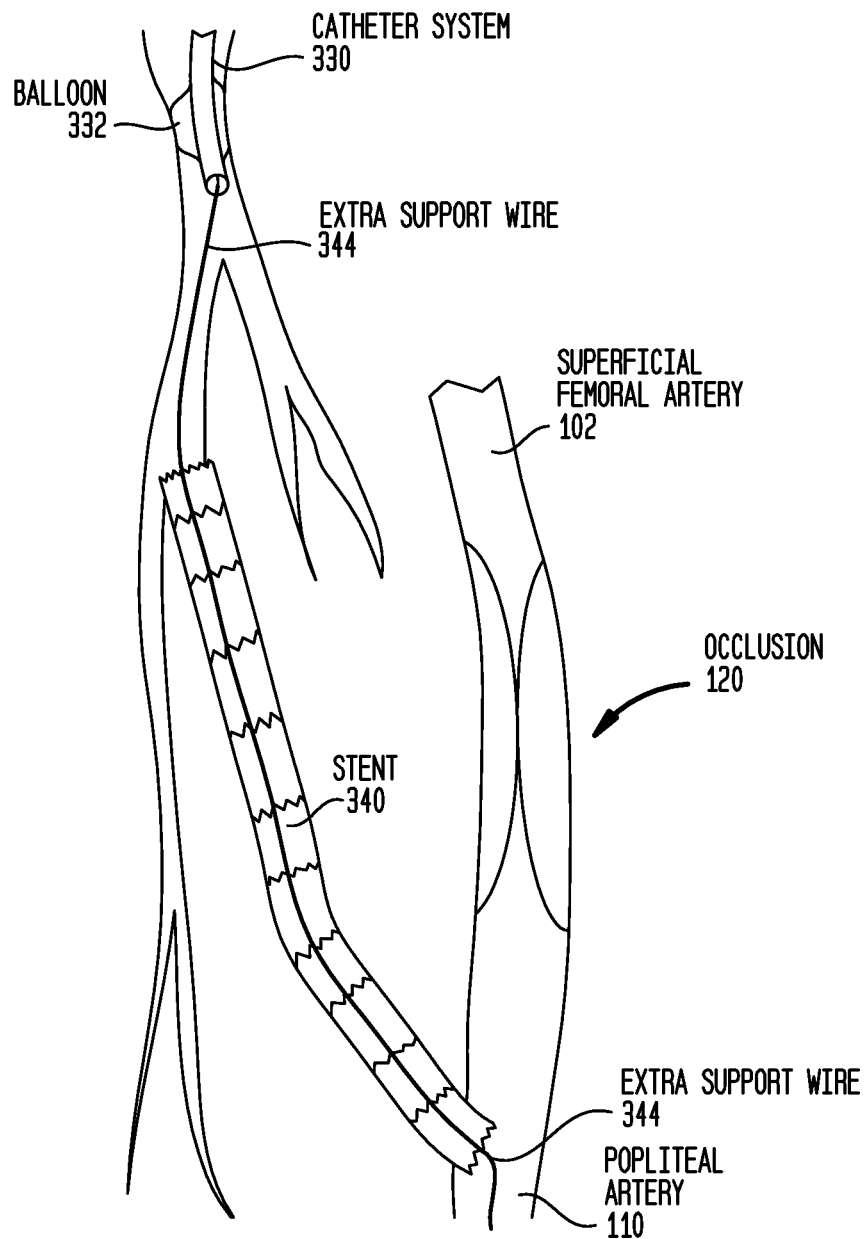
FIG. 3D is schematic, further enlarged view of only a portion of the cardiovascular region of FIG. 3A illustrating the implanted location of a bypass conduit, in accordance with embodiments of the present invention.

As noted above, in medical procedure 200 of FIG. 2A, a bypass conduit is implanted in prepared collateral vessel 108. FIG. 3D illustrates an exemplary implanted position of a bypass conduit 340. For ease of illustration, collateral vessel 108 has been omitted from FIG. 3D. As previously noted, preparation of a selected collateral vessel may damage or destroy the selected vessel. As such, implantation of bypass conduit 340 into a prepared vessel does not necessarily require that the conduit be deployed inside or within the collateral vessel (as would be the case during the deployment of vascular stents inside the lumen of a vessel). Rather, bypass conduit 340 is deployed inside or within the prepared track or channel defined by the prepared and dilated collateral vessel. The bypass conduit creates a new pathway that allows blood to flow from one vascular bed to the organs and tissues originally supplied by SFA 102. In other words, the selected collateral 108 provides the pathway that allows the surgeon to extend the bypass conduit to target vessel 110.

Bypass conduit 340 is implanted in collateral vessel 108 using a delivery system in accordance with embodiments of the present invention. The delivery system is introduced through the lumen in catheter system 330 and then extended along the course of the wire (i.e. along the original course of collateral vessel 108). As described in greater detail below with reference to FIG. 6, the delivery system retains bypass conduit 340 in a contracted (folded) configuration during insertion. Also as described below, bypass conduit 340 is elongated along the delivery system to allow its deployment in its most elongated state. Once the delivery system is positioned in the channel defined by collateral vessel 108, bypass conduit 340 is expanded into a deployed position so as to provide sufficient patency of vessel 110. Following deployment of bypass conduit 340, all balloons are deflated and guide-wire 334, support wire 344 and all components are removed from the patient to enable blood flow through bypass conduit 340.

Evaluation of the adequacy of the blood flow through bypass conduit 340, as well as the adequacy of the deployment of the stent may be performed through one or more additional procedures. For example, if the bypass conduit is not fully expanded, an additional balloon may be used to dilate it further and allow complete expansion. Additionally, the bypass conduit may be evaluated to ensure that there are no leaks of blood along insertion points of the bypass structure into source and target vessels. If present, a leak is addressed appropriately using further balloon dilatation or other means.

Figure 3E:
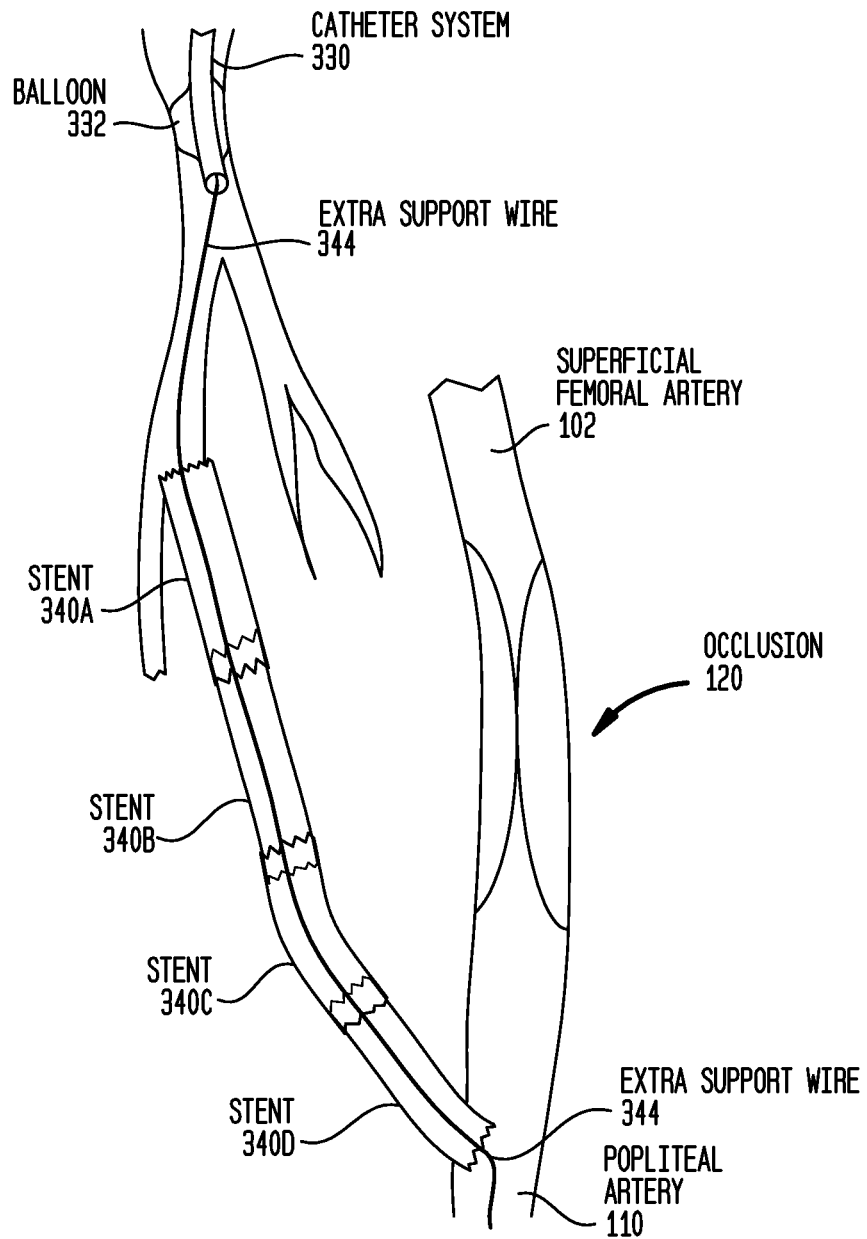
FIG. 3E is schematic, further enlarged view of only a portion of the cardiovascular region of FIG. 3A illustrating the implanted location of a plurality of overlapping bypass conduits, in accordance with embodiments of the present invention.

FIG. 3E illustrates an alternative embodiment of the present invention in which a plurality of overlapping bypass conduits 340 are implanted in collateral vessel 108. As shown, in these embodiments, bypass conduits 340A-D may be sequentially implanted to maintain patency of collateral vessel 108. Again, for ease of illustration collateral vessel 108 has been omitted from FIG. 3E.

FIG. 4A is side view of a bypass conduit 440 in accordance with embodiments of the present invention. In these illustrative embodiments, bypass conduit 440 comprises three portions 452, referred to as source portion 452A, body portion 452B and target portion 452C. Source portion 452A is configured to be implanted in a source vessel, such as vessel 104 of the embodiments of FIGS. 3A-3E, while target portion 452C is configured to be implanted in a target vessel, such as vessel 102 in FIGS. 3A-3E.

In the embodiments of FIG. 4A, body portion 452B includes a fabric covering. The fabric covering allows blood to flow from the source vessel to the target vessel without leaking out of the bypass conduit. The covering does not impede the extension and contraction of the conduit and constitutes the wall of the bypass channel. Source and target portions 452A, 452B are implanted inside an existing blood vessel and, as such, do not require such covering. Body portion 452B may also include hooks 470 disposed on its outer surface. These allow bypass conduit 440 to be fixed to the surrounding tissues, thus providing for a more secure placement.

Figure 4B:
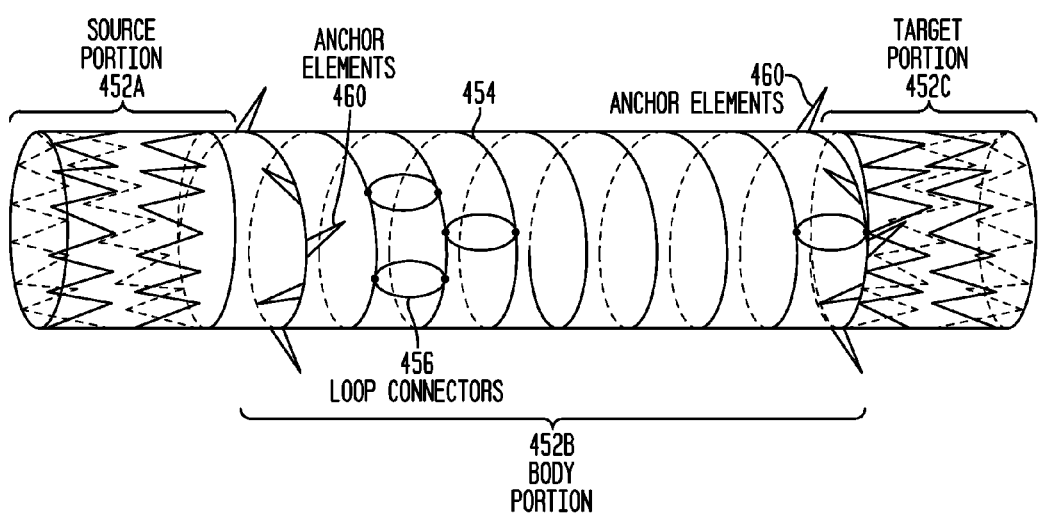
FIG. 4B is a side view of a bypass conduit of FIG. 4A, in accordance with embodiments of the present invention.

Body portion 452B may be of any construction or pattern that can fit the desired function. One such configuration is shown in FIG. 4B. In this arrangement, body portion 452B has a helical wire structure comprising a plurality of contiguous, adjacent turns 454. That is, in the embodiments of FIG. 4B, body portion 452B is formed from a single wire or a plurality of wires connected end-to-end. Due to the helical structure of body portion 452B, it possible for body portion 452B to stretch without comprising the structural integrity of bypass conduit 440. As would be appreciated, the helical wire structure may be formed from a variety of biocompatible metals or polymers. In the embodiments of FIG. 4B, portions 452A and 452C each have a mesh structure, although other structures are within the scope of the present invention.

Figure 4C:
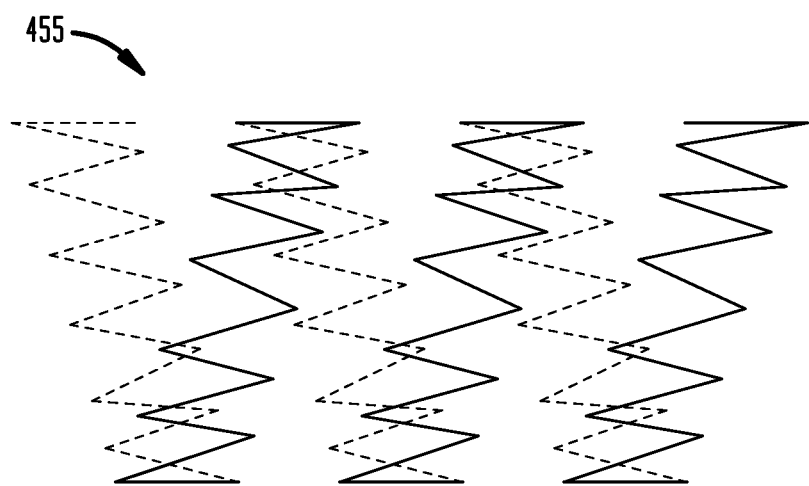
FIG. 4C is a side view of a body portion of a bypass conduit, in accordance with embodiments of the present invention.

In alternative embodiments, the helical wire may be further shaped in a saw-tooth pattern 455 and then rolled into a spiral shape as shown in FIG. 4C. This pattern allows for improved compressibility for storage and delivery, and improved expansion for deployment. Specifically, saw-tooth pattern 455 allows the conduit to fold inward for delivery, and then be expanded outward for deployment.

Figure 5A:
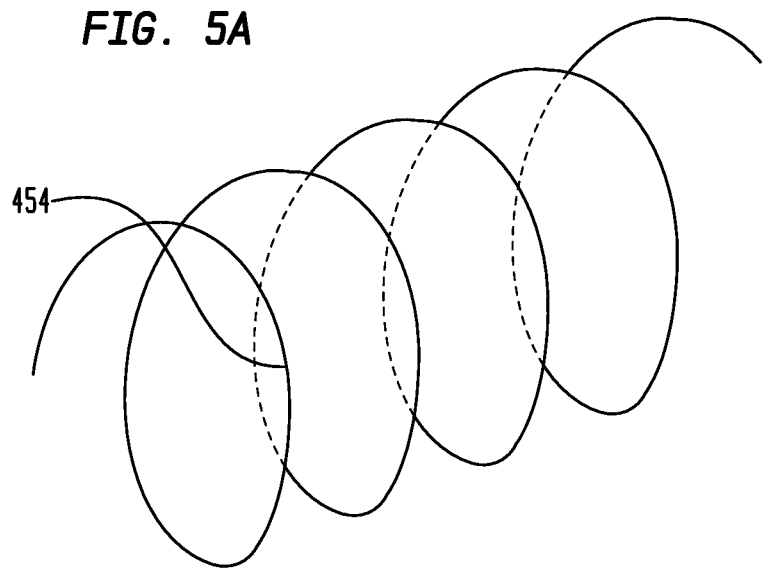
FIG. 5A is a perspective view of the helical wire body of the bypass conduit of FIG. 4, shown in a first configuration, in accordance with embodiments of the present invention.
Figure 5B:
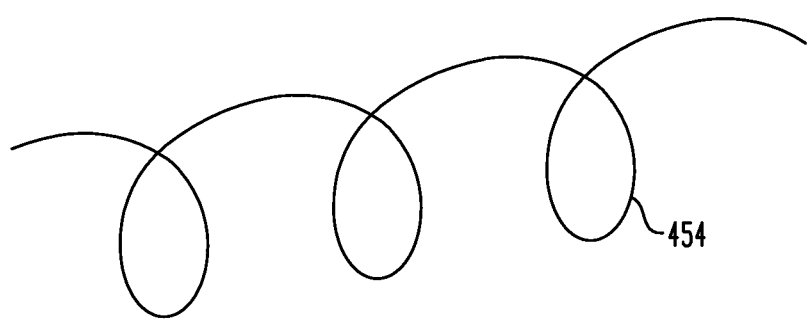
FIG. 5B is a perspective view of the helical wire body of the bypass conduit of FIG. 4, shown in a second configuration, in accordance with embodiments of the present invention.

FIG. 5A is a simplified view of only turns 454 of body portion 452B in which the helical structure is shown in a first, non-stretched or contracted state. In contrast, FIG. 5B illustrates the helical structure formed by turns 454 in a second, stretched or elongated state. As shown, in the stretched state the diameter of each turn 454 decreases, but the length of body portion 452B increases. This allows the bypass conduit to change in length and diameter as dictated by conditions of the organs or tissues that it supplies. For example, if the bypass conduit is placed in the heart, this property allows it to expand and contract with the motion of the heart during the cardiac cycle.

The successive turns of the helical spiral may be connected together in order to improve the structural integrity of the bypass conduit. Multiple types of connectors may be utilized for this purpose as long as they do not impair the expansion and contraction of the helical structure. In one embodiment shown in FIG. 4B, adjacent turns 454 are connected to one another via loop connectors 456. Loop connectors 456 comprise generally round or oval shaped closed curves extending between turns 454. In the specific embodiments of FIGS. 4-5F, loop connectors 456 have a generally elliptical shape and are sometimes referred to herein as elliptical shaped loop connectors. Loop connectors 456 have sufficient structural integrity to add support to body portion 452B, but still permit elongation of body portion 452B. That is, loop connectors are configured to longitudinally and laterally expand and contract as body portion 452B expands and contracts in both directions. Furthermore, as described further below, in certain embodiments loop connectors 456 are configured to engage bead shaped elements of a tool to permit implantation of the bypass conduit into the collateral vessel.

Figure 5C:
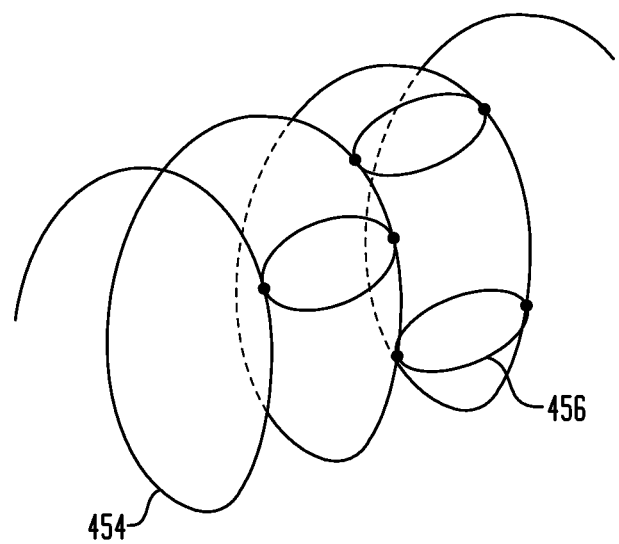
FIG. 5C is a perspective view of the helical wire body and connecting loops of the bypass conduit of FIG. 4, shown in a first configuration, in accordance with embodiments of the present invention.
Figure 5D:
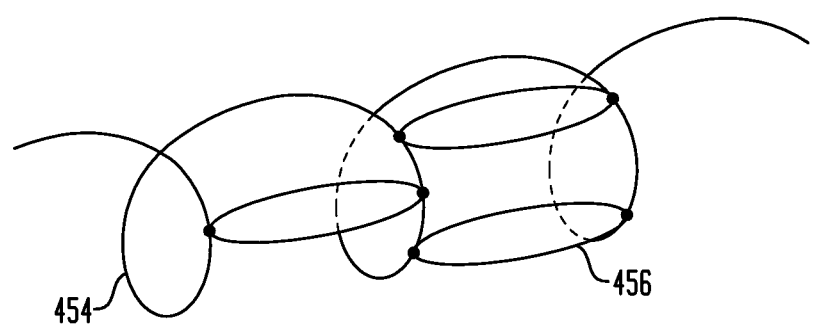
FIG. 5D is a perspective view of the helical wire body and connecting loops of the bypass conduit of FIG. 4, shown in a second configuration, in accordance with embodiments of the present invention.

FIG. 5C is a simplified view of turns 454 and loop connectors 456 in which body portion 452B is in first, non-stretched or contracted state. In contrast, FIG. 5D illustrates the turns 454 and loop connectors 456 in a second, stretched or elongated state. For ease of illustration, only a few loop connectors 456 are shown in FIGS. 4 and 5C-5D.

Figure 5E:
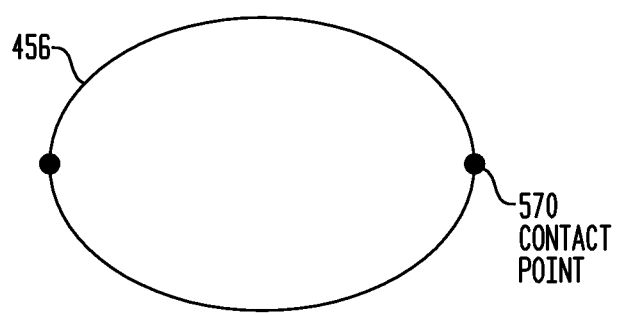
FIG. 5E is a top view of a connector loop of FIG. 4, in accordance with embodiments of the present invention.
Figure 5F:
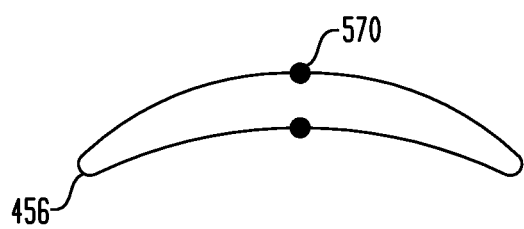
FIG. 5F is a side view of an connector loop of FIG. 4, in accordance with embodiments of the present invention.

FIGS. 5E and 5F are top and side views, respectively of elliptical shaped loop connectors 456. As shown, the opposing apexes of each connector 456 are each connected to a turn 456 at contact points 570 and may have a curvature that maintains the circular cross-sectional shape of bypass conduit 440.

Figure 5G:
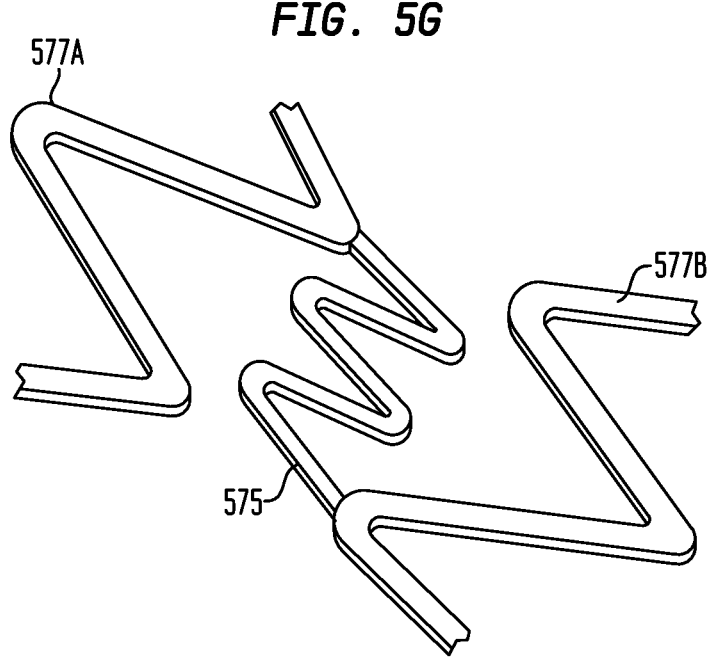
FIG. 5G is a perspective view of an Z-shaped connector, in accordance with embodiments of the present invention.
Figure 5H:
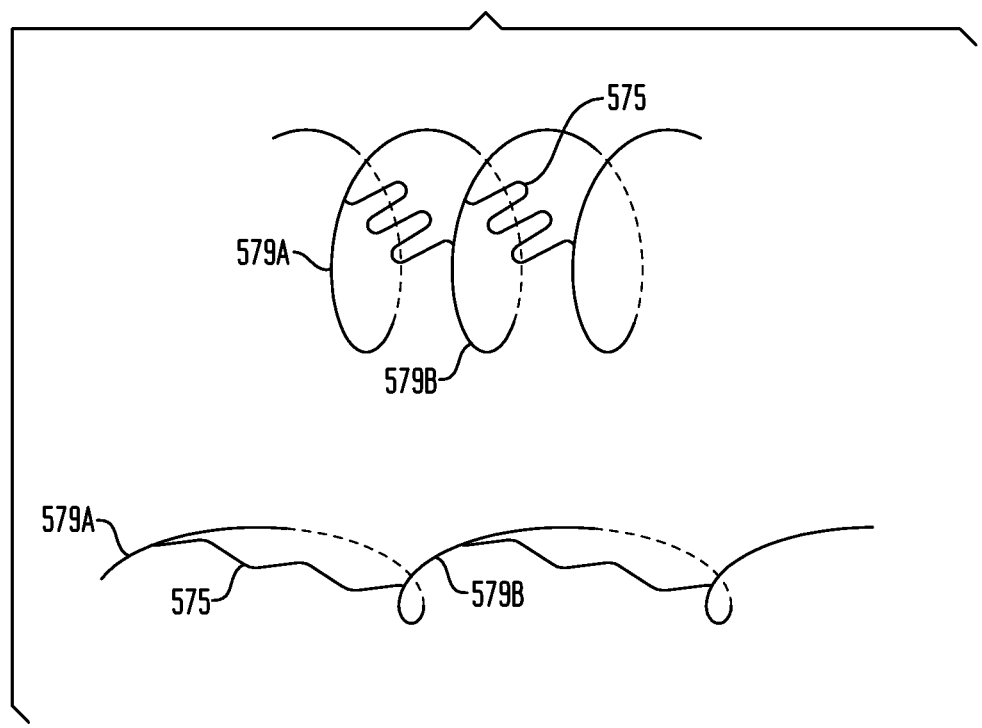
FIG. 5H is a perspective view of helical turns of a bypass conduit connected by a Z-shaped connector, in accordance with embodiments of the present invention.

An alternative to a loop connector are Z-shaped connectors 575. FIG. 5G is a perspective view of a Z-shaped connector 575 between two saw-tooth shaped elements 577. FIG. 5H is a perspective view of helical turns 579 of a bypass conduit connected by Z-shaped connector 575. FIG. 5H shows turns 579 and connector 575 in a contracted state (top figure), and in an elongated state (bottom figure).

It would be appreciated that elliptical-shaped connectors and Z-shaped connectors are not mutually exclusive in the construction of a bypass conduit. Additionally, these two shapes are merely illustrative and are not restrictive of the type of connectors that may be implemented.

Returning to FIG. 4, bypass conduit 440 further comprises a plurality of anchor elements 460 disposed at each end of body portion 452B. Anchoring elements 460 assist in securing the target and source portions 452 within the target and source vessels, respectively. Anchoring elements 460 shown in FIG. 4 comprise spikes. However, it would be appreciated that other anchoring element arrangements may also be implemented in conjunction within, or to substitute for, the anchoring elements 460 shown in FIG. 4.

In certain embodiments, one or more portions 452 may also include a cover. In one specific embodiment, body portion 452B is covered with an elastic fabric material, such as spandex. Covering portions 452 with such a flexible material allows portions 452 to extend and contract, as needed.

Figure 6:
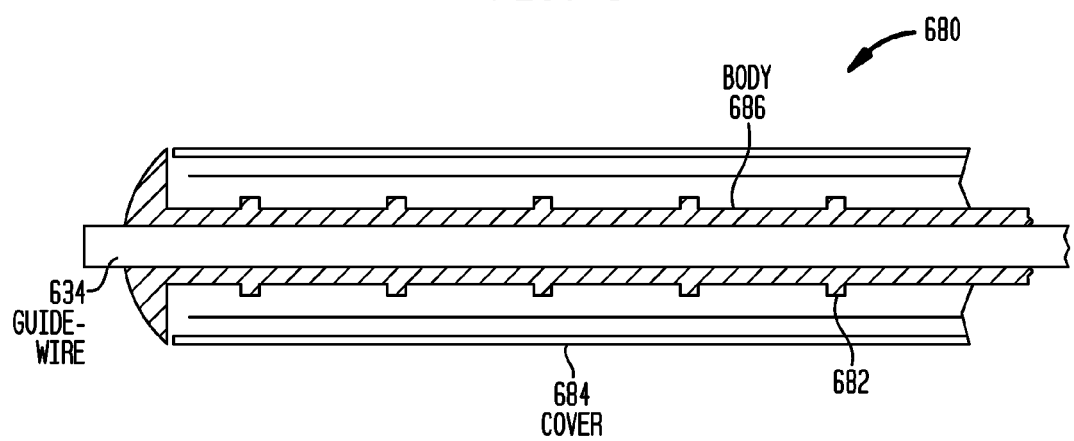
FIG. 6 is a side view of an apparatus for delivering a bypass conduit into a selected collateral vessel, in accordance with embodiments of the present invention.

As noted above, bypass conduit 440 may be implanted in a selected collateral vessel through the use of a delivery system. FIG. 6 is a side view of one exemplary delivery system 680 which may be used to implant bypass conduit 440 of FIG. 4. As shown, delivery system 680 comprises a body 686 which is inserted through a lumen in a catheter system, such as system 330 described above. Body 684 moves along an implanted guide-wire 634.

Also as shown, body 686 has a plurality of beads or ridges 682 disposed thereon. Bypass conduit 440 is placed onto body 686 in an elongated state such that beads 682 engage the stretched loop connectors 456 to retain the loop connectors in the elongate state. Once elongated bypass conduit is positioned on body 686 and retained by beads 682, a retraceable cover 684 is placed thereon. The ridges or beads 682 are one exemplary device for retaining the conduit in an elongated or stretched state while folded in delivery mechanism 680.

When body 686 is properly positioned in the channel defined by the collateral vessel, cover 684 is retracted so that loop connectors 456 are released from beads 682. As such, turns 454 assume a deployed or non-stretched state. Delivery system 680 may then be removed, or used to delivery additional bypass conduits as described above.

During delivery of bypass conduit 440, care may be taken to deliver the anchoring elements 460 in the target vessel and the source vessel as the device is being deployed. Adjustment by advancement or retraction of delivery system 680 may be required during deployment to ensure a correct position. The anchor elements 460 are placed in the source and target vessels together with the source and target portions 452A and 452C respectively.

Figure 7A:
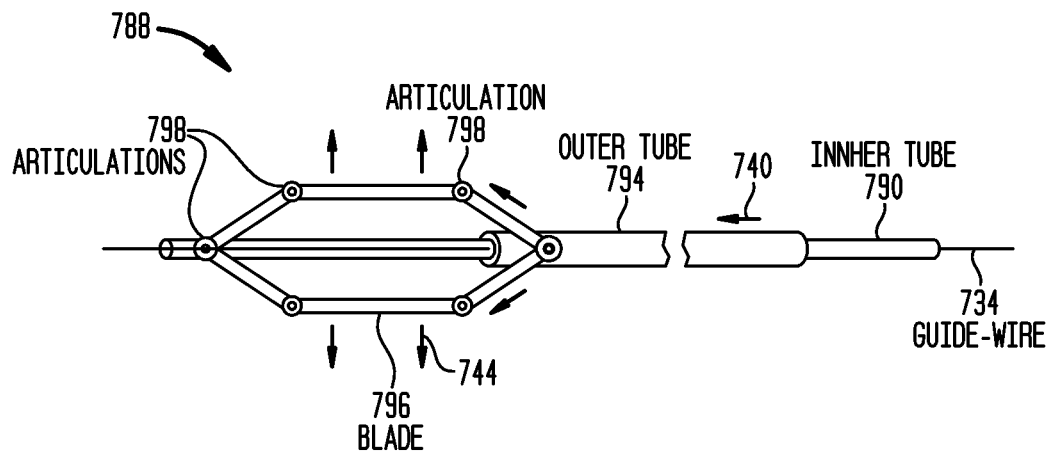
FIG. 7A is side view of a tissue dissector, shown in a first configuration, which may be used in embodiments of the present invention.
Figure 7B:
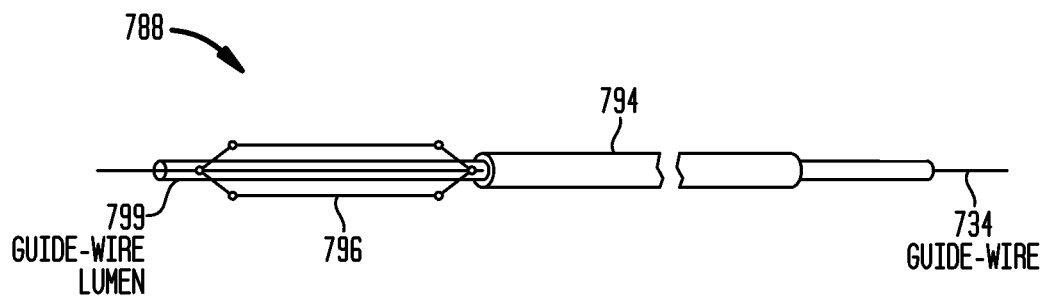
FIG. 7B is side view of a tissue dissector, shown in a second configuration, which may be used in embodiments of the present invention.

As noted above, a collateral vessel is dilated before implantation of a bypass conduit into the remnants thereof. Also as noted, a number of different approaches may be used to dilate a collateral vessel, including through the use of a tissue dissector. FIGS. 7A and 7B are side views on one exemplary tissue dissector 788 which may be used in embodiments of the present invention. FIG. 7A illustrates tissue dissector 788 in an open or deployed configuration while FIG. 7B illustrates the dissector in a closed configuration.

As shown, tissue dissector 788 comprises an inner tube 790 which may move along a guide-wire 734. Tissue dissector 788 also comprises a blade system 792 comprising a plurality of blades 796, and an outer tube 794. Actuation of outer tube 794 in the direction of arrow 740 causes blades 796 to expand outwards in the direction of arrows 742. Articulation mechanisms 798 allow controlled rotation of blades 796. Tissue dissector 788 incorporates a wire lumen 799 that allows the dissector to be advanced over guide-wire 734 to the desired position.

As previously noted, a bypass conduit in accordance with embodiments of the present invention may be implanted through the use of a delivery catheter, such as catheter 330 noted above. FIG. 8 is a top view of one embodiment of delivery catheter 330 having a lumen 821 therein. As shown, delivery catheter 300 includes an occlusion balloon 804 positioned at or near the distal tip of delivery catheter 330. The inflation and deflation of balloon is controlled by injecting fluid or gas through balloon inflation port 803 which is connected to the balloon via lumen 805. A Luer lock, for instance, may be used at infusion port 803 in order to allow balloon 804 to remain inflated for a desired period of time. Proximal tip 807 of catheter 830 may also include a one way valve 802 that prevents blood from bleeding out of the catheter. The catheter may be advanced into position over the guide wire with the use of a tissue dilator (not shown) in a manner similar to a vascular access sheath, which are well-known to the experts in the art of percutaneous endovascular procedures. Catheter 330 also includes a catheter lumen infusion port 801.

FIG. 9 shows an illustration of support wire 344 noted above. Wire 344 is used to occlude the access site to the target vessel during the construction of the channel in order to prevent internal back bleeding. Wire includes an occlusion balloon 903 that is inflated in order to occlude the arteriotomy site of the target vessel. Balloon inflation port 901 is used to inflate the balloon with fluid or gas, and is connected to the balloon via lumen 909. Inflation port 901 may incorporate a locking mechanism in order to maintain balloon 903 in the inflated or deflated position for the desired period of time. As would be appreciated, wire 344 may be sufficiently thin in order to accommodate the different types of equipment (balloons, dissectors, conduits, etc) that are needed to create the channel.

Figure 10:
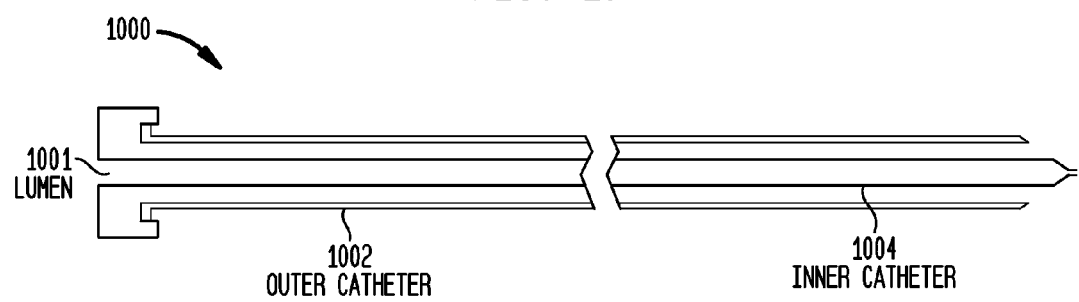
FIG. 10 is a side view of a catheter exchange device which may be implemented with embodiments of the present invention.

The initial wire that is advanced across the collateral vessel has a diameter wire (e.g. 0.014 inch wire) and ends in a distal tip 905. This wire allows small balloons to be passed along to start creating the channel. When larger balloons, tissue dissectors, etc. are needed, a larger support wire may be introduced. This may be accomplished using a catheter exchange device 1000 shown FIG. 10. More specifically, one inner catheter 1004 with a small lumen 1001 may track over the thin wire. An outer catheter 1002 with a larger lumen may track over the inner catheter. The two catheters 1002, 1004 are locked together and are advanced over the small caliber wire. Once the distal tip of the catheters are in the target vessel, inner catheter 1004 is removed together with the small caliber wire, and outer catheter 1002 remains in place. The support wire is advanced into the target vessel through the lumen of the outer catheter. Once the tip of the wire is in the target vessel, the outer catheter 1002 may then be removed and construction of bypass channel may continue. This example of the simple catheter design is merely provided for illustration purposes.

While various embodiments of the present invention have been described above, it should be understood that they have been presented by way of example only, and not limitation. For example, as noted above, intra-cardiac applications are within the scope of the present invention. In an exemplary such embodiment, access may be obtained via a subxiphoid approach in order to place a drain in the pericardial cavity prior to starting the procedure. Furthermore, percutaneous cardiopulmonary bypass may be needed and/or the heart may be fibrillated to prevent motion during the procedure. The remainder of the procedure may continue as described above.

It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method for performing a percutaneous bypass of a diseased vessel of a patient's cardiovascular system, comprising:

destroying a selected, non-diseased collateral vessel so that the selected, non-diseased collateral vessel is prepared to receive at least one bypass conduit comprising a helical wire body having connectors that connect adjacent turns of the helical body; and implanting the at least one bypass conduit into the remnants of the selected, non-diseased collateral vessel so that the at least one bypass conduit maintains a patency sufficient to substitute for the diseased vessel.

2. The method of claim 1, wherein preparing a collateral vessel comprises:

positioning a distal tip of a catheter system within the cardiovascular system upstream from the selected, non-diseased collateral vessel;

advancing a guide-wire from the catheter system through the selected, non-diseased collateral vessel;

stopping the flow of blood into the selected, non-diseased collateral vessel; and dilating the selected, non-diseased collateral vessel to destroy the selected, non-diseased collateral vessel.

3. The method of claim 2, further comprising:

inflating a balloon disposed at the distal tip of the catheter system to cause cessation of blood flow into the selected, non-diseased collateral vessel.

4. The method of claim 1, further comprising:

locating the selected, non-diseased collateral vessel using an imaging device.

5. The method of claim 1, wherein two or more bypass conduits are implanted into the selected, non-diseased collateral vessel.

6. The method of claim 1, wherein the at least one bypass conduit comprises one more anchoring elements disposed on an outer surface of the bypass conduit, and wherein the method further comprises:

anchoring the at least one bypass conduit to the patient using the anchoring elements.

7. The method of claim 6, wherein the anchoring elements are embedded into the tissue surrounding the implanted at least one bypass conduit.

8. The method of claim 1, wherein implanting the bypass conduit comprises:

placing the bypass conduit on a delivery system comprising a plurality of ridges configured to engage one or more loop connectors of the at least one bypass conduit and maintain the at least one bypass conduit in a stretched state;

inserting the delivery system into the selected, non-diseased collateral vessel; and releasing the one or more loop connectors from the ridges so that the at least one bypass conduit is expanded.

9. The method of claim 1, wherein the step of destroying a selected, non-diseased collateral vessel further includes destroying the selected, non-diseased collateral vessel with a tissue dissector.

10. The method of claim 1, further comprising:

inflating a balloon incorporated into a guide-wire during the procedure to prevent back bleeding into the selected, non-diseased collateral vessel.

11. The method of claim 1, wherein the step of destroying a selected, non-diseased collateral vessel further includes sequentially dilating the selected collateral vessel.

12. A method for performing a percutaneous bypass of a diseased vessel portion of a patient's cardiovascular system, comprising:

destroying a portion of a selected collateral vessel so that the portion of the selected collateral vessel is prepared to receive at least one bypass conduit comprising a helical wire body having connectors that connect adjacent turns of the helical body; and implanting the at least one bypass conduit into the remnants of the portion of the selected collateral vessel so that the at least one bypass conduit maintains a patency sufficient to substitute for the diseased vessel;

wherein the location of the destroyed portion of the selected collateral vessel is different than the location of the diseased vessel portion.

* * * * *